US011166894B2

(12) United States Patent
Marsh et al.

(10) Patent No.: US 11,166,894 B2
(45) **Date of Patent: *Nov. 9, 2021**

(54) SHAMPOO COMPOSITIONS COMPRISING A CHELANT

(71) Applicant: The Procter & Gamble Company, Cincinnati, OH (US)

(72) Inventors: Jennifer Mary Marsh, Deerfield Township, OH (US); Casey Patrick Kelly, Wyoming, OH (US); Mark Robert Sivik, Mason, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/515,821

(22) Filed: Jul. 18, 2019

(65) Prior Publication Data

US 2019/0336426 A1 Nov. 7, 2019

Related U.S. Application Data

(63) Continuation of application No. 15/630,411, filed on Jun. 22, 2017, now abandoned.

(60) Provisional application No. 62/356,943, filed on Jun. 30, 2016.

(51) Int. Cl.

*A61K 8/41* (2006.01)
*A61Q 5/02* (2006.01)
*A61K 8/44* (2006.01)
*A61K 8/46* (2006.01)
*A61Q 5/00* (2006.01)

(52) U.S. Cl.

CPC .................. *A61K 8/41* (2013.01); *A61K 8/44* (2013.01); *A61K 8/463* (2013.01); *A61Q 5/002* (2013.01); *A61Q 5/02* (2013.01); *A61K 2800/51* (2013.01); *A61K 2800/596* (2013.01); *A61K 2800/5922* (2013.01)

(58) Field of Classification Search

None

See application file for complete search history.

(56) References Cited

U.S. PATENT DOCUMENTS

| | | | |
|---|---|---|---|
| 3,940,482 | A | 2/1976 | Grand |
| 4,089,945 | A | 5/1978 | Brinkman et al. |
| 4,185,106 | A | 1/1980 | Dittmar et al. |
| 4,321,156 | A | 3/1982 | Bushman |
| 4,412,943 | A | 11/1983 | Hirota et al. |
| 4,749,507 | A | 6/1988 | Varco |
| 4,822,604 | A | 4/1989 | Knoll et al. |
| 4,855,130 | A | 8/1989 | Konrad et al. |
| 5,306,489 | A | 4/1994 | Goldberg et al. |
| 5,559,092 | A | 9/1996 | Gibson et al. |
| 5,635,167 | A | 6/1997 | Said et al. |
| 5,804,172 | A | 9/1998 | Ault |
| 5,847,003 | A | 12/1998 | Ptchelintsev et al. |
| 6,069,169 | A | 5/2000 | Ptchelintsev et al. |
| 6,071,962 | A | 6/2000 | Ptchelintsev et al. |
| 6,287,547 | B1 | 9/2001 | Oota et al. |
| 6,348,189 | B1 | 2/2002 | Tanabe et al. |
| 6,358,502 | B1 | 3/2002 | Tanabe et al. |
| 6,365,143 | B1 | 4/2002 | Lundmark et al. |
| 6,380,263 | B1 | 4/2002 | Pruche et al. |
| 6,432,147 | B1 | 8/2002 | Dias et al. |
| 6,432,394 | B2 | 8/2002 | Pyles et al. |
| 6,509,011 | B1 | 1/2003 | Ellis et al. |
| 6,544,500 | B1 | 4/2003 | O'Toole et al. |
| 6,551,361 | B1 | 4/2003 | Cornwell et al. |
| 6,602,493 | B2 | 8/2003 | Akhter et al. |
| 6,624,126 | B1 | 9/2003 | Kasuga et al. |
| 6,743,434 | B1 | 6/2004 | Lundmark et al. |
| 6,858,202 | B2 | 2/2005 | Niemiec et al. |
| 6,864,314 | B1 | 3/2005 | Yeung et al. |
| 6,927,196 | B2 | 8/2005 | Snyder et al. |
| 7,045,493 | B2 | 5/2006 | Wang et al. |
| 7,169,743 | B2 | 1/2007 | Wang et al. |
| 7,186,274 | B2 | 3/2007 | Vic et al. |
| 7,186,275 | B2 | 3/2007 | Boswell |
| 7,300,647 | B1 | 11/2007 | O'Toole et al. |
| 7,335,700 | B2 | 2/2008 | Yeung et al. |
| 7,547,454 | B2 | 6/2009 | Gupta |
| 7,700,078 | B2 | 4/2010 | Huglin et al. |
| 7,709,430 | B2 | 5/2010 | Mizushima |
| 7,745,382 | B2 | 6/2010 | Sloan |
| 7,915,212 | B2 | 3/2011 | Yeung et al. |
| 8,022,020 | B2 | 9/2011 | Sloan |
| 8,039,424 | B2 | 10/2011 | Sloan |
| 8,404,257 | B1 | 3/2013 | Huglin et al. |

(Continued)

FOREIGN PATENT DOCUMENTS

| | | | |
|---|---|---|---|
| CA | 1147262 | A | 5/1983 |
| DE | 19536420 | A1 | 4/1996 |

(Continued)

OTHER PUBLICATIONS

All final and non-final office actions for U.S. Appl. No. 13/737,035.
All final and non-final office actions for U.S. Appl. No. 13/920,171.
All final and non-final office actions for U.S. Appl. No. 15/630,411.
All final and non-final office actions for U.S. Appl. No. 15/630,426.
All final and non-final office actions for U.S. Appl. No. 15/630,431.
All final and non-final office actions for U.S. Appl. No. 15/630,437.
All final and non-final office actions for U.S. Appl. No. 15/630,899.

(Continued)

*Primary Examiner* — David J Blanchard
*Assistant Examiner* — Sarah J Chickos
(74) *Attorney, Agent, or Firm* — Angela K. Haughey

(57) ABSTRACT

Described herein is a shampoo composition and methods of using the same, the shampoo composition including a copper chelant, a detersive surfactant, and a carrier.

20 Claims, No Drawings

(56) References Cited

U.S. PATENT DOCUMENTS

| | | | |
|---|---|---|---|
| 8,449,868 | B2 | 5/2013 | Jennings et al. |
| 8,637,489 | B2 | 1/2014 | Van Nguyen et al. |
| 8,942,481 | B2 | 1/2015 | Suarez Cambre et al. |
| 9,044,413 | B2 | 6/2015 | Yeung et al. |
| 9,080,135 | B2 | 7/2015 | Hough et al. |
| 9,271,908 | B2 | 3/2016 | Allef et al. |
| 9,358,195 | B2 | 6/2016 | Lupia et al. |
| 9,586,063 | B2 | 3/2017 | Marsh et al. |
| 9,642,788 | B2 | 5/2017 | Marsh et al. |
| 10,539,872 | B2 | 1/2020 | Tadokoro |
| 2003/0095938 | A1 | 5/2003 | Casero |
| 2003/0125224 | A1 | 7/2003 | Seitz, Jr. et al. |
| 2003/0176303 | A1 | 9/2003 | Niemiec et al. |
| 2003/0211953 | A1 | 11/2003 | Glenn et al. |
| 2003/0215522 | A1 | 11/2003 | Johnson et al. |
| 2004/0058855 | A1 | 3/2004 | Schwartz et al. |
| 2004/0123402 | A1 | 7/2004 | Marsh et al. |
| 2004/0261198 | A1 | 12/2004 | Kainz et al. |
| 2004/0266656 | A1 | 12/2004 | Sakurai |
| 2005/0095215 | A1 | 5/2005 | Popp |
| 2005/0095261 | A1 | 5/2005 | Popp |
| 2005/0239723 | A1 | 10/2005 | Amin |
| 2005/0256313 | A1 | 11/2005 | Norenberg et al. |
| 2006/0009371 | A1 | 1/2006 | Wang et al. |
| 2006/0063695 | A1 | 3/2006 | Wang et al. |
| 2006/0130246 | A1 | 6/2006 | Molenda et al. |
| 2006/0287219 | A1 | 12/2006 | Dykstra |
| 2008/0005715 | A1 | 1/2008 | Shimizu et al. |
| 2008/0057015 | A1 | 3/2008 | Oblong et al. |
| 2008/0145328 | A1 | 6/2008 | Schwartz |
| 2009/0071493 | A1 | 3/2009 | Nguyen |
| 2009/0074700 | A1 | 3/2009 | Nguyen et al. |
| 2009/0092561 | A1 | 4/2009 | Lupia et al. |
| 2009/0119852 | A1 | 5/2009 | Marsh |
| 2010/0069338 | A1 | 3/2010 | Ward et al. |
| 2010/0195039 | A1 | 8/2010 | Park |
| 2011/0015120 | A1 | 1/2011 | Bortolin |
| 2012/0034181 | A1 | 2/2012 | Hoffmann et al. |
| 2012/0034182 | A1 | 2/2012 | Hoffmann et al. |
| 2013/0122070 | A1 | 5/2013 | Barnett |
| 2013/0174863 | A1 | 7/2013 | Marsh et al. |
| 2013/0333715 | A1 | 12/2013 | Hutton, III et al. |
| 2014/0079660 | A1 | 3/2014 | Doi |
| 2014/0213499 | A1 | 7/2014 | Chen et al. |
| 2014/0349902 | A1 | 11/2014 | Allef et al. |
| 2015/0011449 | A1 | 1/2015 | Snyder et al. |
| 2015/0030644 | A1 | 1/2015 | Oh et al. |
| 2015/0093420 | A1 | 4/2015 | Snyder et al. |
| 2015/0140052 | A1 | 5/2015 | Gizaw |
| 2015/0182431 | A1 | 7/2015 | Chaudhuri |
| 2016/0175210 | A1 | 6/2016 | Marsh et al. |
| 2018/0000705 | A1 | 1/2018 | Marsh et al. |
| 2018/0000706 | A1 | 1/2018 | Marsh |
| 2018/0000713 | A1 | 1/2018 | Marsh |
| 2018/0000714 | A1 | 1/2018 | Marsh |
| 2018/0000715 | A1 | 1/2018 | Marsh |
| 2020/0345607 | A1 | 11/2020 | Marsh et al. |
| 2020/0360254 | A1 | 11/2020 | Marsh |

FOREIGN PATENT DOCUMENTS

| | | | |
|---|---|---|---|
| DE | 10259199 | A1 | 6/2004 |
| DE | 102011079664 | A1 | 4/2012 |
| EP | 1046390 | A1 | 10/2000 |
| EP | 1714634 | A1 | 10/2006 |
| EP | 2067467 | A2 | 6/2009 |
| FR | 2853529 | A1 | 10/2004 |
| FR | 2853530 | A1 | 10/2004 |
| FR | 2853531 | A1 | 10/2004 |
| GB | 2288812 | A | 1/1995 |
| GB | 2315770 | A | 2/1998 |
| JP | S57109711 | A | 7/1982 |
| JP | S63150213 | A | 6/1988 |
| JP | 05262623 | | 10/1993 |
| JP | 06041579 | | 2/1994 |
| JP | H07258698 | A | 10/1995 |
| JP | H091 83996 | A | 7/1997 |
| JP | H09291024 | A | 11/1997 |
| JP | H11139941 | A | 5/1999 |
| JP | 11180836 | A | 7/1999 |
| JP | 11269487 | | 10/1999 |
| JP | 2004059540 | | 2/2004 |
| JP | 2006160708 | A | 6/2006 |
| JP | 2008169183 | | 7/2008 |
| JP | 2011046652 | | 3/2011 |
| KR | 1020090077562 | A | 7/2009 |
| WO | WO9116878 | A1 | 11/1991 |
| WO | WO9311737 | A1 | 6/1993 |
| WO | WO9804237 | A1 | 2/1998 |
| WO | WO9824400 | A2 | 6/1998 |
| WO | WO0051555 | A1 | 9/2000 |
| WO | WO0051556 | A1 | 9/2000 |
| WO | WO200119327 | A1 | 3/2001 |
| WO | WO0220486 | A2 | 3/2002 |
| WO | WO02065982 | A2 | 8/2002 |
| WO | WO02102302 | A2 | 12/2002 |
| WO | WO2007079793 | A1 | 7/2007 |
| WO | WO2008136000 | A2 | 11/2008 |
| WO | WO2008153050 | A1 | 12/2008 |
| WO | WO 2010/106342 | * | 9/2010 |
| WO | WO201220226 | A1 | 2/2012 |
| WO | WO2012021472 | A1 | 2/2012 |
| WO | WO2014182766 | A1 | 11/2014 |

OTHER PUBLICATIONS

Gary W. Evans, "The Role of Picolinic acid in Metal Metabolism", Life Chemistry Reports, Jan. 1, 1982, pp. 57-67.

PCT International Search Report and Written Opinion for PCT/US2013/020735 dated Aug. 5, 2013.

PCT International Search Report and Written Opinion for PCT/US2017/038897 dated Sep. 18, 2017.

PCT International Search Report and Written Opinion for PCT/US2017/038899 dated Aug. 21, 2017.

PCT International Search Report and Written Opinion for PCT/US2017/038900 dated Aug. 21, 2017.

PCT International Search Report and Written Opinion for PCT/US2017/038903 dated Sep. 25, 2017.

PCT International Search Report and Written Opinion for PCT/US2017/038904 dated Sep. 18, 2017.

Vitality Unlimited: "What's a Picolinate?—Picolinic acid is the body's prime natural chelator", Dec. 30, 1989.

Zurowska Bogum Ed—Lippert Bernhard et al, "Structural and Magnetic characterization of Cu-picolinate and Cu-Quinaldinate nad their mixed complexes with water or halides", Inorganica Chimica Acta, vol. 418, May 2, 2014, pp. 136-152.

Alberto Culver, Canada, Shampoo, Mintel GNPD, Mar. 2008.

All final and non-final office actions for U.S. Appl. No. 16/931,880.

All final and non-final office actions for U.S. Appl. No. 16/985,902.

Procter & Gamble, UK, 0% Grease Shampoo, Mintel, Feb. 2016.

Charles N Reilley et al.: "Chelan Approach to Analysis (I) Survey of Theory and Application", Journal of Chemical Education, Nov. 1, 1959 (Nov. 1, 1959), XP0557 40258,Retrieved from the Internet:URL:https://pubs.acs.org/doi/pdf/10.1021/ed036p555?rand=jisnuiqf [retrieved on Oct. 15, 2020], pp. 555-564.

* cited by examiner

SHAMPOO COMPOSITIONS COMPRISING A CHELANT

FIELD OF THE INVENTION

Described herein are shampoo compositions comprising a detersive surfactant, a chelant, and a carrier, wherein the shampoo composition inhibits both deposition/penetration of copper salts and other transition metal salts in the hair and removes such salts from hair fiber. A method of cleansing hair with such shampoo compositions is also described herein.

BACKGROUND OF THE INVENTION

Many water sources that are used by consumers for personal care contain elevated levels of calcium and magnesium salts, as well as undesirable levels of redox metals (e.g., copper and/or iron) salts. As such, using chelants to sequester trace redox metals often proves to be ineffective because most chelants also competitively bind calcium and/or magnesium.

It has been found that even trace quantities of copper can deposit on the hair surface and in between the cuticle layers of hair. This deposition of copper on hair is especially problematic because transition metal ions, such as copper and iron, can facilitate reduction-oxidation (redox) reactions during hair coloring treatments and during UV exposure. These reactions generate reactive oxygen species (ROS), which in turn can cause damage to the hair. In addition, they can interfere with the oxidative color formation chemistry and lead to reduced color uptake for hair colorant users.

Accordingly, there is a need for improved shampoo compositions that can inhibit copper depositing on hair, as well as facilitate the removal of copper already deposited thereon.

SUMMARY OF THE INVENTION

Described herein is a shampoo composition comprising: (a) from about 0.005% to about 5% of one or more chelants, by weight of the shampoo composition, wherein the one or more chelants have a molecular structure as follows:

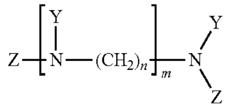

wherein n is 2 or 3; m is 1, 2, 3, or 4; and

Y and Z are independently selected from the group consisting of hydrogen, methyl, ethyl, propyl, butyl, pentyl, $—CH_2CH_2OH$, $—CH_2CH(CH_3)OH)$, $—CH_2CH_2NH_2$, $—CH_2CH(CH_3)\ NH_2$, and combinations thereof;

and wherein the one or more chelants comprise:

(1) log of the formation constant log $K_{ML}$ of its complex with copper is higher than 6;

(2) log P value is from about −5 to about 2; and (3) molecular weight of from about 50 to about 500;

(b) from about 2% to about 50% of one or more detersive surfactants, by weight of the shampoo composition; and (c) from about 75% to about 98% of an aqueous carrier, by weight of the shampoo composition;

wherein the shampoo composition has a pH of about 3 to about 8.

DETAILED DESCRIPTION OF THE INVENTION

While the specification concludes with claims particularly pointing out and distinctly claiming the invention, it is believed that the shampoo composition described herein will be better understood from the following description.

As used herein, the term "fluid" includes liquids and gels.

As used herein, the term "log x" refers to the common (or decadic) logarithm of x.

As used herein, the articles including "a" and "an" when used in a claim, are understood to mean one or more of what is claimed or described.

All percentages are by weight of the total composition, unless stated otherwise. All ratios are weight ratios, unless specifically stated otherwise. All ranges are inclusive and combinable. The number of significant digits conveys neither a limitation on the indicated amounts nor on the accuracy of the measurements. The term "molecular weight" or "M.Wt." as used herein refers to the weight average molecular weight unless otherwise stated. "QS" means sufficient quantity for 100%.

As used herein, "mixtures" is meant to include a simple combination of materials and any compounds that may result from their combination.

All numerical amounts are understood to be modified by the word "about" unless otherwise specifically indicated. Unless otherwise indicated, all measurements are understood to be made at 25° C. and at ambient conditions, where "ambient conditions" means conditions under about one atmosphere of pressure and at about 50% relative humidity. All such weights percents (wt %) as they pertain to listed ingredients are based on the active level and do not include carriers or by-products that may be included in commercially available materials, unless otherwise specified.

Unless otherwise noted, all component or composition levels are in reference to the active portion of that component or composition, and are exclusive of impurities, for example, residual solvents or by-products, which may be present in commercially available sources of such components or compositions.

Herein, "comprising" means that other steps and other ingredients which do not affect the end result can be added. This term encompasses the terms "consisting of" and "consisting essentially of". The compositions, methods, uses, kits, and processes of the shampoo composition described herein can comprise, consist of, and consist essentially of the elements and limitations of the invention described herein, as well as any of the additional or optional ingredients, components, steps, or limitations described herein. As used herein, the terms "include," "includes," and "including," are meant to be non-limiting and are understood to mean "comprise," "comprises," and "comprising," respectively.

The term "substantially free from" or "substantially free of" as used herein means less than about 1%, or less than about 0.8%, or less than about 0.5%, or less than about 0.3%, or about 0%, by total weight of the composition.

"Hair," as used herein, means mammalian hair including scalp hair, facial hair and body hair, particularly on hair on the human head and scalp.

"Cosmetically acceptable," as used herein, means that the compositions, formulations or components described are suitable for use in contact with human keratinous tissue without undue toxicity, incompatibility, instability, allergic response, and the like. All compositions described herein which have the purpose of being directly applied to keratinous tissue are limited to those being cosmetically acceptable.

"Derivatives," as used herein, includes but is not limited to, amide, ether, ester, amino, carboxyl, acetyl, acid, and/or alcohol derivatives of a given compound.

"Polymer," as used herein, means a chemical formed from the polymerisation of two or more monomers, which may be the same or different. The term "polymer" as used herein shall include all materials made by the polymerisation of monomers as well as natural polymers.

Polymers made from only one type of monomer are called homopolymers. A polymer comprises at least two monomers. Polymers made from two or more different types of monomers are called copolymers. The distribution of the different monomers can be calculated statistically or block-wise—both possibilities are suitable for the shampoo composition. Except if stated otherwise, the term "polymer" used herein includes any type of polymer including homopolymers and copolymers.

The term "charge density" as used herein, means the ratio of the number of positive charges on a monomeric unit of which a polymer is comprised to the M.Wt. of said monomeric unit. The charge density multiplied by the polymer M.Wt. determines the number of positively charged sites on a given polymer chain. For cationic guars, charge density is measured using standard elemental analysis of percentage nitrogen known to one skilled in the art. This value of percentage nitrogen, corrected for total protein analysis, can then be used to calculate the number or equivalence of positive charges per gram of polymer. For the cationic copolymers, the charge density is a function of the monomers used in the synthesis. Standard NMR techniques know to one skilled in the art would be used to confirm that ratio of cationic and non-ionic monomers in the polymer. This would then be used to calculate the number or equivalence of positive charges per gram of polymer. Once these values are know, the charge density is reported in milliequivalence (meq) per gram of cationic polymer.

The term log P is the n-octanol/water partition coefficients of the material.

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Shampoo Composition

Described herein is a shampoo composition comprising (a) from about 0.005% to about 5% of one or more chelants; (b) from about 2% to about 50% of one or more detersive surfactants, by weight of the shampoo composition; (c) from about 75% to about 98% of an aqueous carrier, by weight of the shampoo composition, wherein the shampoo composition has a pH of about 3 to about 8, and wherein the shampoo inhibits copper deposition on hair and facilitates the removal of copper deposited on hair. The shampoo composition also delivers consumer desired shampooing in addition to inhibiting the deposition of copper (i.e. from the water used to rinse) on the hair.

A. Chelants

The shampoo composition comprises from about 0.005% to about 5%, alternatively from about 0.01% to about 3%, alternatively from about 0.01% to about 1%, alternatively from about 0.01% to about 0.5%, alternatively from about 0.01% to about 0.1%, and alternatively from about 0.025% to about 0.05% of one or more chelants by weight of the shampoo composition, wherein the one or more chelants have a molecular structure as follows:

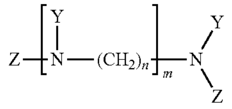

wherein n is 2 or 3; m is 1, 2, 3, or 4; and

Y and Z are independently selected from the group consisting of hydrogen, methyl, ethyl, propyl, butyl, pentyl, $—CH_2CH_2OH$, $—CH_2CH(CH_3)OH)$, $—CH_2CH_2NH_2$, $—CH_2CH(CH_3)\ NH_2$, and combinations thereof;

and wherein the one or more chelants comprise:

(1) log of the formation constant log $K_{ML}$ of its complex with copper is higher than 6;

(2) log P value is from about −5 to about 2; and (3) molecular weight of from about 50 to about 500.

Stability Constants of Exemplary Chelants

The relative affinity of a chelant at a specified pH for $Cu^{+2}$ can be assessed by its Stability Constant. The Stability Constant of a metal chelant interaction is defined as:

$$K_{ML} = \frac{[ML]}{[M][L]}$$

where:

[ML] is the concentration of metal ligand complex at equilibrium;

[M] is the concentration of free metal ion;

[L] is the concentration of free ligand in a fully deprotonated form; and $K_{ML}$ is the stability constant for the metal chelant complex.

The stability constants of chelant-metal ion complexes are well documented in the literature for commonly used chelants (see, for example, Arthur Martell & Robert M Smith, Critically Selected Stability Constants of Metal Complexes Database, Version 3.0 and above, incorporated herein by reference). When not documented the constants can be measured using various analytical methods (see "Metal Complexes in Aqueous Solutions", Martel and Hancock, edition Modem Inorganic Chemistry, p. 226-228, incorporated herein by reference).

It has been found that effective chelants need to have a high affinity for copper in order to preferentially bind copper found in hair. However, it has been found that also important to efficacy is the ability for the chelant to penetrate inside the hair fibers rapidly during the shampoo lathering process (which typically lasts between 30 seconds and 1 minute). The copper to be removed is inside the hair and the chelant needs to penetrate inside hair and form a strong copper-chelant complex. This copper-chelant complex needs to be water soluble and thus easily removed during the rinsing process. To be able to do this, two additional parameters have been shown to be important for chelant efficacy. These are log P, the octanol/water partitioning coefficient, and the molecular weight of the chelant. Both are related to the ability of the chelant to penetrate into hair and also form a water soluble copper-chelant complex The one or more chelants for use in the shampoo composition may be selected from the group consisting of triethylenetetramine, tetraethylenepenatmine, pentaethylenehexamine, tris(2-aminoethyl)amine, ethylenedinitrilotetrapropan-2-ol, 1,1',1"-[[2-hydroxypropyl)imino]bis(2,1-ethanediylnitrilo)]tetrakis-2-propanol, tetraethylenepentaamine-(1-EO), 1,5,9,13-tetraazatridecane, and mixtures thereof.

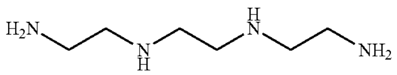

2,3-Triethylenetetramine (TETA)

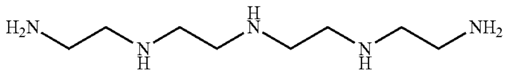

2,4-Tetraethylenepentamine (TEPA)

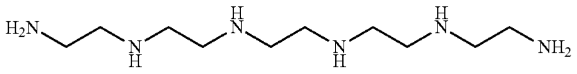

Pentaethylenehexamine (PEHA)

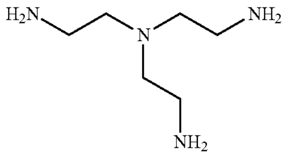

Tris(2-aminoethyl)amine (tren)

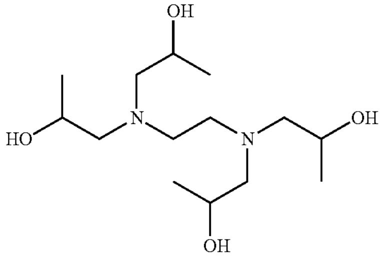

Ethylenedinitrilotetrapropan-2-ol (EDTP)

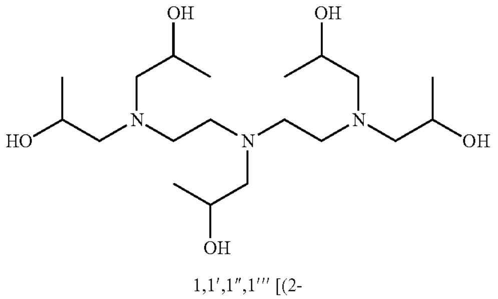

1,1′,1″,1‴ [(2-hydroxypropyl)imino]bis(2,1ethanediylnitrilo)]tetrakis-2-Propanol (Pentrol)

-continued

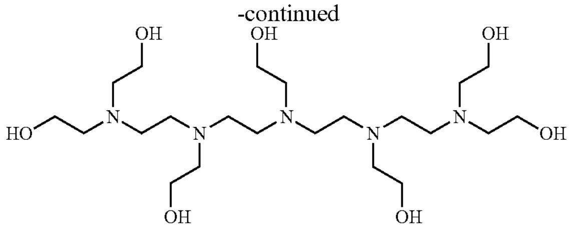

Tetraethylenepentaamine-(1-EO)

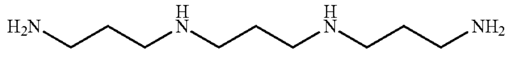

1,5,9,13-Tetraazatridecane

Table 1 provides relevant properties and performance of the one or more copper chelants described herein. Details on determination of copper removing performance is described in the Examples section.

TABLE 1

Properties of representative chelants

| Chelant | Copper Removing Performance from Shampoo | Log $K_{ML}$ Cu | Log P | MW |
|---|---|---|---|---|
| 2,3-Triethylenetetramine (TETA) | 70% | 20.1 | −2.3 | 146 |
| 2,4-Tetraethylenepentamine (TEPA) | 60% | 22.8 | −2.7 | 189 |
| Pentaethylenehexamine (PEHA) | 55% | | −3.1 | 232 |
| Tris(2-aminoethyl)amine (tren) | 45% | 18.8 | −2.2 | 146 |
| Ethylenedinitrilotetrapropan-2-ol (EDTP) | 30% | 9.8 | −0.2 | 292 |
| 1,1,1",1'" [(2-hydroxypropyl)imino] bis(2,1-ethanediylnitrilo)]tetrakis-2-Propanol (Pentrol) | No data collected | | −0.2 | 394 |
| Tetraethylenepentaamine-(1-EO) | No data collected | | −2.9 | 498 |
| 1,5,9,13-Tetraazatridecane (Thermine) | 15% | 17.1 | −2.1 | 188 |

The log of the formation constant log $K_{ML}$ of its complex with copper can be higher than 6, alternatively higher than 8, alternatively higher than 9, alternatively higher than 10, alternatively higher than 12, alternatively higher than 14, alternatively higher than 16, alternatively higher than 17, alternatively higher than 18, and alternatively higher than 20. The log of the formation constant log $K_{ML}$ of its complex with copper can be from about 6 to about 28, alternatively from about 8 to about 27, alternatively from about 9 to about 26, alternatively from about 10 to about 25, alternatively from about 12 to about 24, alternatively from about 14 to about 24, alternatively from about 16 to about 24, alternatively from about 17 to about 24, alternatively from about 18 to about 24, and alternatively from about 20 to about 23.

The log P value of the one or more chelants can be from about −5 to about 2, alternatively from about −4 to about 1, alternatively from about −3.5 to about 0, and alternatively from about −2.9 to about −2.5.

The molecular weight of the one or more chelants can be from about 50 to about 500, alternatively from about 75 to about 400, alternatively from about 100 to about 350, alternatively from about 125 to about 325, alternatively from about 140 to about 300, alternatively from about 140 to about 200.

The copper removing performance of the shampoo composition is determined by treating hair with clarifying shampoo containing the corresponding chelant for 20 cycles and comparing the copper content of the hair compared to the same treatment using shampoo without the chelant.

Other chelants that can be used to reduce copper content of hair have the following general structure:

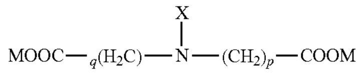

wherein M is hydrogen or a metal ion;

p is 1 or 2;

q is 1 or 2; and

X is selected from the group containing hydrogen, methyl, ethyl, propyl, $—CH_2CH_2OH$, $—CH_2CH(CH_3)OH)$, $—CH_2CH_2NH_2$, $—CH_2CH(CH_3)$ $NH_2$, $—CH_2COOM$, or $—CH_2CH_2SH$, and $—CH_2CH(CH_3)SH)$.

Non-limiting examples include iminodiacetic acid, N-(2-hydroxyethyl)iminodiacetic acid, N-methyliminodiacetic acid, N-(2-aminoethyl)iminodiacetic acid, N-propyliminodiacetic acid, and nitrilotriacetic acid.

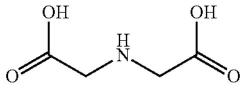

Iminodiacetic acid

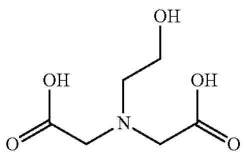

N-(2-Hydroxyethyl)iminodiacetic acid

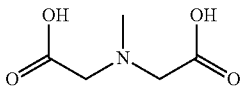

N-Methyliminodiacetic acid

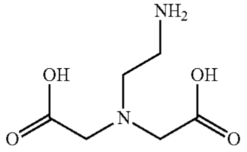

N-(2-Aminoethyl)iminodiacetic acid

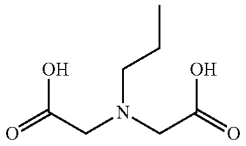

N-Propyliminodiacetic acid

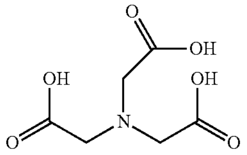

Nitrilotriacetic acid

It is found that treatment with shampoo composition containing 0.1 wt % iminodiacetic acid reduces copper by 40% and shampoo composition containing 0.1 wt % N-(2-hydroxyethyl)iminodiacetic acid reduces copper by 30% after 20 cleaning cycles compared to comparative treatment with shampoo that does not contain the chelant.

B. Detersive Surfactant

The shampoo composition comprises from about 2% to about 50%, alternatively from about 5% to about 25%, alternatively from about 7% to about 22%, alternatively from about 9% to about 18%, and alternatively from about 11% to about 15% of one or more detersive surfactants by weight of the shampoo composition. The concentration of the detersive surfactant component in the shampoo composition should be sufficient to provide the desired cleaning and lather performance.

The one or more detersive surfactants can be selected from the group consisting of anionic surfactants, amphoteric or zwitterionic surfactants, or mixtures thereof. The one or more detersive surfactants can also be selected from the group consisting of anionic surfactants, cationic surfactants, non-ionic surfactants, amphoteric surfactants, and mixtures thereof. Various examples and descriptions of detersive surfactants are set forth in U.S. Pat. No. 6,649,155; U.S. Patent Application Publication No. 2008/0317698; and U.S. Patent Application Publication No. 2008/0206355, which are incorporated herein by reference in their entirety.

Anionic surfactants suitable for use in the compositions are the alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Other similar anionic surfactants are described in U.S. Pat. Nos. 2,486,921; 2,486,922; and 2,396,278, which are incorporated herein by reference in their entirety.

Exemplary anionic surfactants for use in the shampoo composition include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In a further embodiment, the anionic surfactant is sodium lauryl sulfate or sodium laureth sulfate.

Suitable amphoteric or zwitterionic surfactants for use in the shampoo composition include those which are known for use in shampoo or other personal care cleansing. Concentrations of such amphoteric surfactants range from about 0.5 wt % to about 20 wt %, and from about 1 wt % to about 10 wt %. Non limiting examples of suitable zwitterionic or amphoteric surfactants are described in U.S. Pat. Nos. 5,104,646 and 5,106,609, which are incorporated herein by reference in their entirety.

Amphoteric detersive surfactants suitable for use in the shampoo composition include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Exemplary amphoteric detersive surfactants for use in the present shampoo composition include cocoamphoacetate, cocoamphodiacetate, lauroamphoacetate, lauroamphodiacetate, and mixtures thereof.

Zwitterionic detersive surfactants suitable for use in the shampoo composition include those surfactants broadly described as derivatives of aliphatic quaternaryammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. In another embodiment, zwitterionics such as betaines are selected.

Non limiting examples of other anionic, zwitterionic, amphoteric or optional additional surfactants suitable for use in the shampoo composition are described in McCutcheon's, Emulsifiers and Detergents, 1989 Annual, published by M. C. Publishing Co., and U.S. Pat. Nos. 3,929,678, 2,658,072; 2,438,091; 2,528,378, which are incorporated herein by reference in their entirety.

The shampoo composition may also comprise a cationic conditioning polymer, an aqueous carrier, and other additional ingredients described herein.

C. Cationic Conditioning Polymers

The shampoo composition described herein may comprise one or more cationic conditioning polymers. This polymer may be selected from the group consisting of (a) a cationic guar polymer, (b) a cationic non-guar polymer, (c) a cationic tapioca polymer, (d) a cationic copolymer of acrylamide monomers and cationic monomers, (e) a synthetic, non-crosslinked, cationic polymer, which forms lyotropic liquid crystals upon combination with the detersive surfactant, and (f) mixtures thereof.

D. Carrier

The shampoo composition further comprises from about 75% to about 98%, alternatively from about 80% to about 98% of a cosmetically acceptable carrier, by weight of the shampoo composition. The carrier can be an aqueous carrier. The amount and chemistry of the carrier is selected according to the compatibility with other components and other desired characteristic of the product. In an embodiment, the carrier is selected from the group consisting of: water and water solutions of lower alkyl alcohols. Lower alkyl alcohols useful herein are monohydric alcohols having 1 to 6 carbons, such as ethanol and/or isopropanol. In an embodiment, the cosmetically acceptable carrier is a cosmetically acceptable aqueous carrier and is present at a level of from about 20% to about 95%, or from about 60% to about 85%.

The pH of the shampoo composition can be from about pH 3 to about pH 8, alternatively from about pH 4 to about pH 7, and alternatively from about pH 5 to about pH 6.

E. Benefit Agent

The shampoo composition may further comprise one or more benefit agents. Exemplary benefit agents include, but are not limited to, silicone emulsions, anti-dandruff actives, perfume microcapsules, gel networks, colorants, particles, and other insoluble skin or hair conditioning agents such as skin silicones, natural oils such as sun flower oil or castor oil.

(1). Silicone Emulsion

The silicone emulsions suitable for use herein include emulsions of insoluble polysiloxanes prepared in accordance with the descriptions provided in U.S. Pat. No. 4,476,282 and U.S. Patent Application Publication No. 2007/0276087. Accordingly, insoluble polysiloxanes referred to herein for the purpose of the invention include polysiloxanes such as alpha, omega hydroxy-terminated polysiloxanes or alpha, omega alkoxy-terminated polysiloxanes having a molecular weight within the range from about 50,000 to about 500,000 g/mol. As used herein, "insoluble polysiloxane" means that the water solubility of the polysiloxane is less than 0.05 wt %. In another embodiment, the water solubility of the polysiloxane is less than 0.02 wt %, or less than 0.01 wt %, or less than 0.001 wt %. According to an embodiment, the insoluble polysiloxane is present in the shampoo composition in an amount within the range from about 0.1 wt % to about 3 wt %, based on the total weight of the composition. For example, the insoluble polysiloxane can be present in an amount within the range from about 0.2 wt % to about 2.5 wt %, or from about 0.4 wt % to about 2.0 wt %, or from about 0.5 wt % to about 1.5 wt %, based on the total weight of the composition.

According to one aspect of the silicone emulsion, the insoluble polysiloxane used herein include alpha, omega hydroxy- or alkoxy-terminated polysiloxanes having a general formula I:

$$R^1—[O—SiR_2]_n—OR^1,$$

wherein 'n' is an integer, R is a substituted or unsubstituted $C_1$ to $C_{10}$ alkyl or aryl, and $R^1$ is a hydrogen or a substituted or unsubstituted $C_1$ to $C_{10}$ alkyl or aryl. Non-limiting examples of R and $R^1$ may be independently selected from alkyl groups such as methyl, ethyl, n-propyl, isopropyl, n-butyl, isobutyl, tert-butyl, n-pentyl, isopentyl, neopentyl, tertpentyl, hexyl such as n-hexyl, heptyl such as n-heptyl, octyl such as n-octyl and isooctyl such as 2,2,4-trimethylpentyl, nonyl such as n-nonyl, decyl such as n-decyl, dodecyl such as n-dodecyl, octadecyl such as n-octadecyl; or aryl groups such as phenyl, naphthyl, anthryl and phenanthryl. In an embodiment, the insoluble polysiloxane has a general formula $H—[O—SiR_2]_n—OH$.

According to another aspect of the silicone emulsion, the insoluble polysiloxane has an average molecular weight within the range from about 50,000 to about 500,000 g/mol. For example, the insoluble polysiloxane may have an average molecular weight within the range from about 60,000 to about 400,000; from about 75,000 to about 300,000; from about 100,000 to about 200,000; or the average molecular weight may be about 150,000 g/mol.

According to another aspect of the silicon emulsion, total content of a cyclic polysiloxane having a general formula:

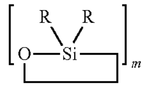

wherein R is as defined above, and wherein m is 4 or 5, is present in the silicone emulsion in an amount less than about 2.5 wt % based on the total weight of all polysiloxanes. For example, dimethiconol may include significant quantities of cyclic polysiloxanes, such as octamethylcyclotetrasiloxane (D4) and decamethylcyclotetrasiloxane (D5). In an embodiment, the amount of D4 is less than about 2.0%, or less than about 1.5%, or less than about 1.0%, or less than about 0.5%, based on the total weight of all polysiloxanes. In an embodiment, the amount of D5 is less than about 0.5%, or less than about 0.4%, or less than about 0.3%, or less than about 0.2%, based on the total weight of all polysiloxanes.

According to yet another aspect of the silicone emulsion, the emulsion has a viscosity up to about 500,000 cPs. For example, the viscosity may be within the range from about 75,000 to about 300,000, from about 100,000 to about 200,000, or about 150,000 cPs.

According to yet another aspect of the silicone emulsion, the insoluble polysiloxane has an average particle size within the range from about 30 nm to about 10 micron. The average particle size may be within the range from about 40 nm to about 5 micron, from about 50 nm to about lmicron, from about 75 nm to about 500 nm, or about 100 nm, for example.

The average molecular weight of the insoluble polysiloxane, the viscosity of the silicone emulsion, and the size of the particle comprising the insoluble polysiloxane are determined by methods commonly used by those skilled in the art, such as the methods disclosed in Smith, A. L. *The Analytical Chemistry of Silicones*, John Wiley & Sons, Inc.: New York, 1991. For example, the viscosity of the silicone emulsion can be measured at 30° C. with a Brookfield viscosimeter with spindle 6 at 2.5 rpm.

According to another aspect of the silicone emulsion, the emulsion further includes an anionic surfactant that participates in providing high internal phase viscosity emulsions having particle sizes in the range from about 30 nm to about 10 micron. The anionic surfactant is selected from organic sulfonic acids. Most common sulfonic acids used in the present process are alkylaryl sulfonic acid; alkylaryl polyoxyethylene sulphonic acid; alkyl sulfonic acid; and alkyl polyoxyethylene sulfonic acid. General formulas of the sulfonic acids are as shown below:

$R^2C_6H_4SO_3H$ (II)

$R^2C_6H_4O(C_2H_4O)_mSO_3H$ (III)

$R^2SO_3H$ (IV)

$R^2O(C_2H_4O)_mSO_3H$ (IV)

Where $R^2$, which may differ, is a monovalent hydrocarbon radical having at least 6 carbon atoms. Non-limiting examples of $R^2$ include hexyl, octyl, decyl, dodecyl, cetyl, stearyl, myristyl, and oleyl. 'm' is an integer from 1 to 25. Exemplary anionic surfactants include but are not limited to octylbenzene sulfonic acid; dodecylbenzene sulfonic acid; cetylbenzene sulfonic acid; alpha-octyl sulfonic acid; alpha-dodecyl sulfonic acid; alpha-cetyl sulfonic acid; polyoxyethylene octylbenzene sulfonic acid; polyoxyethylene dodecylbenzene sulfonic acid; polyoxyethylene cetylbenzene sulfonic acid; polyoxyethylene octyl sulfonic acid; polyoxyethylene dodecyl sulfonic acid; and polyoxyethylene cetyl sulfonic acid. Generally, 1 to 15% anionic surfactant is used in the emulsion process. For example, 3-10% anionic surfactant can be used to obtain an optimum result.

The silicone emulsion may further include an additional emulsifier together with the anionic surfactant, which along with the controlled temperature of emulsification and polymerization, facilitates making the emulsion in a simple and faster way. Non-ionic emulsifiers having a hydrophilic lipophilic balance (HLB) value of 10 to 19 are suitable and include polyoxyalkylene alkyl ether, polyoxyalkylene alkylphenyl ethers and polyoxyalkylene sorbitan esters. Some useful emulsifiers having an HLB value of 10 to 19 include, but are not limited to, polyethylene glycol octyl ether; polyethylene glycol lauryl ether; polyethylene glycol tridecyl ether; polyethylene glycol cetyl ether; polyethylene glycol stearyl ether; polyethylene glycol nonylphenyl ether; polyethylene glycol dodecylphenyl ether; polyethylene glycol cetylphenyl ether; polyethylene glycol stearylphenyl ether; polyethylene glycol sorbitan monostearate; and polyethylene glycol sorbitan monooleate.

In accordance with another embodiment, the composition may further comprise an anti-dandruff active, which may be an anti-dandruff active particulate.

F. Other Components

The shampoo composition can also additionally comprise any suitable optional ingredients as desired. Such optional ingredients should be physically and chemically compatible with the components of the composition, and should not otherwise unduly impair product stability, aesthetics, or performance. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of nonlimiting materials that can be added to the composition herein.

In accordance with another embodiment of the invention, a method of making a shampoo composition comprising a detersive surfactant, a cationic conditioning polymer, a chelant, and a carrier is provided. The method includes (i) combining the detersive surfactant and the cationic conditioning polymer in suitable carrier, and (ii) combining a chelant and a carrier composition that includes a product of step (i) to form the shampoo composition.

In an embodiment, the shampoo composition has a viscosity of 4,000 cP to 20,000 cP, or from about 6,000 cP to about 12,000 cP, or from about 8,000 cP to about 11,000 cP, measured at 26.6° C. with a Brookfield R/S Plus Rheometer at 2 $s^{-1}$. cP means centipoises.

Also described herein is a method of inhibiting copper deposition on hair and facilitating the removal of copper deposited on hair comprising applying to the hair a shampomo composition described herein and rinsing the shampoo composition from the hair.

Inhibition of copper deposition on hair and facilitation of the removal of copper deposited on hair may also be achieved by applying a leave-on treatment to the hair after rinsing the conditioner from the hair. The leave-on treatment may deliver consumer desired conditioning in addition to inhibiting the deposition of copper (i.e. from the water used to rinse) on the hair. The leave-on treatment described herein may comprise from about 0.025% to about 0.50%, alternatively from about 0.05% to about 0.25% of one or more chelants described herein, by weight of the leave-on treatment. The leave-on treatment may also comprise one or more rheology modifiers and an aqueous carrier.

The shampoo composition can be prepared by conventional formulation and mixing techniques. It will be appreciated that other modifications of the shampoo composition within the skill of those in the hair care formulation art can be undertaken without departing from the spirit and scope of this invention. All parts, percentages, and ratios herein are by weight unless otherwise specified. Some components may come from suppliers as dilute solutions. The amount stated reflects the weight percent of the active material, unless otherwise specified.

Test Methods

Shampoo Treatment Protocol

All testing are performed on colored hair switches (see Method of Measurement of Copper on Hair below) weighing approximately 4.0 grams and having a length of approximately 6 inches. The hair switches are commercially available from IHIP (International Hair Importers). Three hair switches per sampoo composition are used. An amount of 0.20 g of shampoo is spread via a syringe onto separate hair switch. That is, the dosage is 0.10 g of shampoo per g of hair. Each application consists of adding shampoo to the hair, milking for 30 seconds followed by rinsing for 30 seconds. Shampoo is then reapplied (0.1 g/g), milked for 30 seconds and rinsed for 30 seconds. Excess water is squeezed from the hair switches and left to air dry or treated with a rinse-off conditioner and/or a leave-on treatment composition. This protocol is repeated for a number of times/cycles (as indicated in the tables below, which describe the details of hair treatments).

Method of Measurement of Copper on Hair

The following test method is used to assess the ability of the compositions and regimens to remove copper from the hair and to inhibit copper deposition onto the hair.

Hair switches are colored once with an oxidative hair colorant. An extra blonde shade is used for the testing. The hair switches are washed for 10 or 20 repeat wash cycles in tap water containing 7 grains per gallon water hardness (Ca/Mg) and 0.06 μg/g copper ions. Each wash cycle consists of two applications of 0.1 g/g a shampoo to the hair switches. Each application consists of adding shampoo to the hair, milking for 30 secs followed by rinsing for 30 secs. Shampoo is then reapplied 0.1 g/g, milked for 30 secs, rinsed for 30 secs and then dried in a heat box (60° C.) until dry.

Samples of 100 mg of hair are digested overnight with 2 ml of high purity concentrated nitric acid. The digestive mixture also contains 150 μL of 100 μg/g Yttrium internal standard (Inorganic Ventures, Christianburg, Va., USA). Following digestion, samples are heated to 70-80° C. for one hour, cooled to room temperature and diluted to 15 mL with deionized water. Copper content of the hair switches is determined by inductively coupled plasma atomic spectroscopy (ICP-OES)). For each leg, 3 different samples are analyzed.

EXAMPLES & DATA

The following are non-limiting examples of the shampoo composition described herein. The examples are given solely for the purpose of illustration and are not to be construed as limitations of the shampoo composition, as many variations thereof are possible without departing from the spirit and scope of the shampoo composition, which would be recognized by one of ordinary skill in the art.

The shampoo composition described herein is generally prepared by conventional methods. Such methods typically involve mixing of the ingredients in one or more steps to a relatively uniform state, with or without heating, cooling, application of vacuum, and the like. The compositions are prepared such as to optimize stability (physical stability, chemical stability, photostability) and/or delivery of the active materials. The shampoo composition may be in a single phase or a single product, or the shampoo composition may be in a separate phases or separate products. If two products are used, the products may be used together, at the same time, or sequentially. Sequential use may occur in a short period of time, such as immediately after the use of one product, or it may occur over a period of hours or days.

In order to minimize the variability of the resulting copper content on hair that is related to (a) lot-to-lot viariability due to hair switches and (b) day-to-day variability of the water used during shampoo and conditioner treatments, a single lot of hair switches is used for each experimental series and a separate control experiment/treatment is run for each experimental series (see below).

Experimental Series I

Investigation of treatments with clarifying shampoos containing simple surfactants and 2,3-Triethylenetetramine.

| Components | Ex. 1 Control Wt % | Ex. 2 Wt % |
|---|---|---|
| Sodium Laureth-1 Sulfate[1] | 10.50 | 10.50 |
| Sodium Lauryl Sulfate[2] | 1.50 | 1.50 |
| Cocamidopropyl betaine | 1.00 | 1.00 |
| Sodium benzoate | 0.25 | 0.25 |
| Citric Acid | 0.70 | 0.70 |
| Methylchloroisothiazolinone/ Methylisothiazolinone[3] | 0.0005 | 0.0005 |
| Sodium chloride | 1.00 | 1.00 |
| Tetrasodium EDTA dihydrate | 0.16 | 0.16 |

-continued

| Components | Ex. 1 Control Wt % | Ex. 2 Wt % |
|---|---|---|
| 2,3-Triethylenetetramine (TETA) | 0.00 | 0.10 |
| Deionized water | Q.S. | Q.S. |
| pH adjusted to | 6.0 | 6.0 |

[1]Sodium laureth-3-sulfate available from BASF as Standapol ES-3 (28 wt. % active).
[2]Sodium Lauryl Sulfate available from BASF as Standapol WAQ-LC (29 wt. % active).
[3]Kathon CG available from Dow (1.5 wt % active).

Results of Experimental Series I

| Composition of | Ex. 1 | Ex. 2 |
|---|---|---|
| Summary Description of Composition | Control Clarifying shampoo with simple surfactant | Clarifying shampoo with simple surfactant and chelant |
| Concentration of Chelant in Shampoo | 0.0% | 0.10% |
| Chelant used | — | 2,3-Triethylenetetramine |
| Shampoo pH | 6.0 | 6.0 |
| Shampoo cycles | 10 | 10 |
| Average final copper concentration in hair (ppm) | 84 | 33 |
| Standard deviation | 4.2 | 1.1 |
| Relative content of Copper content on hair after treatment (versus control shampoo treatment) | 100 | 33 |

Chelant 2,3-Triethylenetetramine contributes to significant reduction of copper content on hair after 10 shampoo cycle treatments compared to treatment with shampoo composition that does not comprise the chelant.

Experimental Series II

Investigation of treatments with clarifying shampoos containing simple surfactants and 2,3-Triethylenetetramine in two different pH values.

| Components | Ex. 3 Control Wt % | Ex. 4 Control Wt % | Ex. 5 Wt % | Ex. 6 Wt % |
|---|---|---|---|---|
| Sodium Laureth-1 Sulfate[1] | 10.50 | 10.50 | 10.50 | 10.50 |
| Sodium Lauryl Sulfate[2] | 1.50 | 1.50 | 1.50 | 1.50 |
| Cocamidopropyl betaine | 1.00 | 1.00 | 1.00 | 1.00 |
| Sodium benzoate | 0.25 | 0.25 | 0.25 | 0.25 |
| Citric Acid | 0.70 | 1.00 | 0.70 | 1.00 |
| Methylchloroisothiazolinone/ Methylisothiazolinone[3] | 0.0005 | 0.0005 | 0.0005 | 0.0005 |
| Sodium chloride | 1.00 | 1.00 | 1.00 | 1.00 |
| Tetrasodium EDTA dihydrate | 0.16 | 0.16 | 0.16 | 0.16 |
| 2,3-Triethylenetetramine | 0.00 | 0.00 | 0.10 | 0.10 |
| Deionized water | Q.S. to 100 | Q.S. to 100 | Q.S. to 100 | Q.S. to 100 |
| pH adjusted to | 6.0 | 4.25 | 6.0 | 4.25 |

[1]Sodium laureth-3-sulfate available from BASF as Standapol ES-3 (28 wt. % active).
[2]Sodium Lauryl Sulfate available from BASF as Standapol WAQ-LC (29 wt. % active).
[3]Kathon CG available from Dow (1.5 wt % active).

Results of Experimental Series II

| Composition of | Ex. 3 | Ex. 4 | Ex. 5 | Ex. 6 |
|---|---|---|---|---|
| Summary Description of Composition | Control Clarifying shampoo with simple surfactant | Control Clarifying shampoo with simple surfactant | Clarifying shampoo with simple surfactant and chelant | Clarifying shampoo with simple surfactant and chelant |
| Concentration of Chelant in Shampoo | 0.0% | 0.0% | 0.10% | 0.10% |
| Chelant used | — | — | 2,3-Triethylenetetramine | 2,3-Triethylenetetramine |
| Shampoo pH | 6.0 | 4.25 | 6.0 | 4.25 |
| Shampoo cycles | 20 | 20 | 20 | 20 |
| Average final copper concentration in hair (ppm) | 92 | 62 | 34 | 36 |
| Standard deviation | 11 | 4.8 | 3.1 | 3.6 |
| Relative content of Copper content on hair after treatment (versus control shampoo treatment) | 100.0 | 67 v. Control | 39 v. Control | 37 v. Control |

The presence of 2,3-Triethylenetetramine acid contributes to an effective removal of copper from hair after 20 shampoo cycles both at low and a higher pH value. Without the chelant, lower pH shows higher copper removal from hair.

Experimental Series III

Investigation of treatments with clarifying shampoos containing simple surfactants (pH=6) and various chelants described herein.

| Components | Ex. 7 Control Wt % | Ex. 8 Wt % | Ex. 9 Wt % | Ex. 10 Wt % | Ex. 11 Wt % |
|---|---|---|---|---|---|
| Sodium Laureth-1 Sulfate[1] | 10.50 | 10.50 | 10.50 | 10.50 | 10.50 |
| Sodium Lauryl Sulfate[2] | 1.50 | 1.50 | 1.50 | 1.50 | 1.50 |
| Cocamidopropyl betaine | 1.00 | 1.00 | 1.00 | 1.00 | 1.00 |
| Sodium benzoate | 0.25 | 0.25 | 0.25 | 0.25 | 0.25 |
| Citric Acid | 0.70 | 0.70 | 0.70 | 1.00 | 1.00 |
| Methylchloroisothiazolinone/ Methylisothiazolinone[3] | 0.0005 | 0.0005 | 0.0005 | 0.0005 | 0.0005 |
| Sodium chloride | 1.00 | 1.00 | 1.00 | 1.00 | 1.00 |
| Tetrasodium EDTA dihydrate | 0.16 | 0.16 | 0.16 | 0.16 | 0.16 |
| 2,3-Triethylenetetramine | 0.00 | 0.10 | 0.00 | 0.00 | 0.00 |
| Tetraethylenepentamine | 0.00 | 0.00 | 0.10 | 0.00 | 0.00 |
| Tris(2-aminoethyl)amine | 0.00 | 0.00 | 0.00 | 0.00 | 0.00 |
| Pentaethylenehexamine | 0.00 | 0.00 | 0.00 | 0.00 | 0.10 |
| Deionized water | Q.S. to 100 | Q.S. to 100 | Q.S. to 100 | Q.S. to 100 | Q.S. to 100 |
| pH adjusted to | 6.0 | 6.0 | 6.0 | 6.0 | 6.0 |

[1]Sodium laureth-3-sulfate available from BASF as Standapol ES-3 (28 wt. % active).
[2]Sodium Lauryl Sulfate available from BASF as Standapol WAQ-LC (29 wt. % active).
[3]Kathon CG available from Dow (1.5 wt % active).

Results of Experimental Series III

| Composition of | Ex. 7 | Ex. 8 | Ex. 9 |
|---|---|---|---|
| Summary Description of Composition | Control Clarifying shampoo with simple surfactant | Clarifying shampoo with simple surfactant and chelant | Clarifying shampoo with simple surfactant and chelant |
| Concentration of Chelant in Shampoo | 0.0% | 0.10% | 0.10% |
| Chelant used | — | 2,3-Triethylenetetramine | Tetraethylenepentamine |
| Chelant Class | — | Class III | Class III |
| Shampoo pH | 6.0 | 6.0 | 6.0 |
| Shampoo cycles | 20 | 20 | 20 |

-continued

| | | | |
|---|---|---|---|
| Average final copper concentration in hair (ppm) | 115 | 37 | 49 |
| Standard deviation | 14 | 2.8 | 2.7 |
| Relative content of Copper content on hair after treatment (versus control shampoo treatment) | 100 | 32 | 43 |

| Composition of | Ex. 10 | Ex. 11 |
|---|---|---|
| Summary Description of Composition | Clarifying shampoo with simple surfactant and chelant | Clarifying shampoo with simple surfactant and chelant |
| Concentration of Chelant in Shampoo | 0.10% | 0.10% |
| Chelant used | Tris(2-aminoethyl)amine | Pentaethylenehexamine |
| Shampoo pH | 6.0 | 6.0 |
| Shampoo cycles | 20 | 20 |
| Average final copper concentration in hair (ppm) | 62 | 53 |
| Standard deviation | 3.8 | 10.5 |
| Relative content of Copper content on hair after treatment (versus control shampoo treatment) | 54 | 46 |

All chelants from Class III evaluated in a 20 cycle cleaning treatment using a clarifying shampoo containing simple surfactants shows reduction of copper hair content compared to the control shampoo treatment. 2,3-Triethylenetetramine and Tetraethylenepentamine show more effective treatements.

Experimental Series IV

Investigation of treatments with clarifying shampoos containing simple surfactants (pH=6) and ethylenedinitrilotetrapropan-2-ol chelant.

| Components | Ex. 12 Control Wt % | Ex. 13 Wt % |
|---|---|---|
| Sodium Laureth-1 Sulfate[1] | 10.50 | 10.50 |
| Sodium Lauryl Sulfate[2] | 1.50 | 1.50 |
| Cocamidopropyl betaine | 1.00 | 1.00 |
| Sodium benzoate | 0.25 | 0.25 |
| Citric Acid | 0.70 | 0.70 |
| Methylchloroisothiazolinone/ Methylisothiazolinone[3] | 0.0005 | 0.0005 |
| Sodium chloride | 1.00 | 1.00 |
| Tetrasodium EDTA dihydrate | 0.16 | 0.16 |
| Ethylenedinitrilotetrapropan-2-ol | 0.00 | 0.40 |
| Deionized water | Q.S. to 100 | Q.S. to 100 |
| pH adjusted to | 6.0 | 6.0 |

[1]Sodium laureth-3-sulfate available from BASF as Standapol ES-3 (28 wt. % active).
[2]Sodium Lauryl Sulfate available from BASF as Standapol WAQ-LC (29 wt. % active).
[3]Kathon CG available from Dow (1.5 wt % active).

Results of Experimental Series IV

| Composition of | Ex. 12 | Ex. 13 |
|---|---|---|
| Summary Description of Composition | Control Clarifying shampoo with simple surfactant | Clarifying shampoo with simple surfactant and chelant |

-continued

| Composition of | Ex. 12 | Ex. 13 |
|---|---|---|
| Concentration of Chelant in Shampoo | 0.00% | 0.40% |
| Chelant used | — | Ethylene-dinitrilotetra-propan-2-ol |
| Shampoo pH | 6.0 | 6.0 |
| Shampoo cycles | 20 | 20 |
| Average final copper concentration in hair (ppm) | 70 | 50 |
| Standard deviation | 2.6 | 0.4 |
| Relative content of Copper content on hair after treatment (versus control shampoo treatment) | 100 | 71 |

The presence of ethylenedinitrilotetrapropan-2-ol acid (at a concentration of 0.40 wt %) contributes to an effective removal of copper from hair after 20 shampoo cycles compared to the corresponding treatment with control shampoo that does not contain the chelant.

Experimental Series V

Investigation of treatments with clarifying shampoos containing simple surfactants, a rheology modifier and tris-2-aminoethylamine.

| Components | Ex. 14 Control Wt % | Ex. 15 Wt % |
|---|---|---|
| Sodium Laureth-3 Sulfate[1] | 6.00 | 6.00 |
| Sodium Lauryl Sulfate[2] | 9.50 | 9.50 |
| Cocamidopropyl betaine | 1.88 | 1.88 |
| Tetrasodium EDTA dihydrate | 0.16 | 0.16 |
| Citric Acid (Anhydrous) | 0.28 | 0.28 |

-continued

| Components | Ex. 14 Control Wt % | Ex. 15 Wt % |
|---|---|---|
| Sodium benzoate | 0.25 | 0.25 |
| Methylchloroisothiazolinone/ Methylisothiazolinone[3] | 0.0005 | 0.0005 |
| Sodium chloride | 0.57 | 0.57 |
| Hydroxypropylmethylcellulose | 0.25 | 0.25 |
| Tris-2-aminoethylamine | 0.00 | 0.10 |
| Perfume | 0.40 | 0.40 |
| Distilled Water | Q.S. | Q.S. |

[1]Sodium laureth-3-sulfate available from BASF as Standapol ES-3 (28 wt. % active).
[2]Sodium Lauryl Sulfate available from BASF as Standapol WAQ-LC (29 wt. % active).
[3]Kathon CG available from Dow (1.5 wt % active).

Results of Experimental Series V

| Composition of | Ex. 14 | Ex. 15 |
|---|---|---|
| Summary Description of Composition | Control Clarifying shampoo with simple surfactant and Rheology Modifier | Clarifying shampoo with simple surfactant, a Rheology Modifier and a chelant |
| Concentration of Chelant in Shampoo | 0.00% | 0.10% |
| Chelant used | — | Tris-2-aminoethylamine |
| Shampoo pH | 6.0 | 6.0 |
| Shampoo cycles | 10 | 10 |
| Average final copper concentration in hair (ppm) | 94 | 62 |
| Standard deviation | 15 | 9.5 |
| Relative content of Copper content on hair after treatment (versus control shampoo treatment) | 100 | 66 |

The presence of tris-2-aminoethylamine acid contributes to an effective removal of copper from hair after 10 shampoo cycles compared to the corresponding treatment with control clarifying shampoo that does not contain the chelant.

Experimental Series VI

Investigation of treatments with clarifying shampoos containing simple surfactants, a rheology modifier and chelants having 2-aminodiacetic acid molecular structures.

| Components | Ex. 16 Control Wt % | Ex. 17 Wt % | Ex. 18 Wt % |
|---|---|---|---|
| Sodium Laureth-3 Sulfate[1] | 6.00 | 6.00 | 6.00 |
| Sodium Lauryl Sulfate[2] | 9.50 | 9.50 | 9.50 |
| Cocamidopropyl betaine | 1.88 | 1.88 | 1.88 |
| Tetrasodium EDTA dihydrate | 0.16 | 0.16 | 0.16 |
| Citric Acid (Anhydrous) | 0.28 | 0.28 | 0.28 |
| Sodium benzoate | 0.25 | 0.25 | 0.25 |
| Methylchloroisothiazolinone/ Methylisothiazolinone[3] | 0.0005 | 0.0005 | 0.0005 |
| Sodium chloride | 0.57 | 0.57 | 0.57 |
| Hydroxypropylmethylcellulose | 0.25 | 0.25 | 0.25 |
| Iminodiacetic acid | 0.00 | 0.10 | 0.00 |
| N-(2-hydroxyethyl)iminodiacetic acid | 0.00 | 0.00 | 0.10 |
| Perfume | 0.40 | 0.40 | 0.40 |
| Distilled Water | Q.S. | Q.S. | Q.S. |

[1]Sodium laureth-3-sulfate available from BASF as Standapol ES-3 (28 wt. % active).
[2]Sodium Lauryl Sulfate available from BASF as Standapol WAQ-LC (29 wt. % active).
[3]Kathon CG available from Dow (1.5 wt % active).

Results of Experimental Series VI

| Composition of | Ex. 16 | Ex. 17 | Ex. 18 |
|---|---|---|---|
| Summary Description of Composition | Control Clarifying shampoo with simple surfactant and Rheology Modifier | Clarifying shampoo with simple surfactant, a Rheology Modifier and a chelant | Clarifying shampoo with simple surfactant, a Rheology Modifier and a chelant |
| Concentration of Chelant in Shampoo | 0.00% | 0.10% | 0.10% |
| Chelant used | — | Iminodiacetic acid | N-(2-hydroxyethyl)iminodiacetic acid |
| Shampoo pH | 6.0 | 6.0 | 6.0 |
| Shampoo cycles | 20 | 20 | 20 |
| Average final copper concentration in hair (ppm) | 84 | 51 | 56 |
| Standard deviation | 6.5 | 2.7 | 1.7 |
| Relative content of Copper content on hair after treatment (versus control shampoo treatment) | 100 | 61 | 67 |

The presence of chelants having 2-aminodiacetic acid molecular structures contributes to an effective removal of copper from hair after 20 shampoo cycles compared to the corresponding treatment with control clarifying shampoo that does not contain the chelant.

Experimental Series VII

Investigation of treatments using shampoos and rinse-off conditioner and leave-on treatments containing 2,3-Triethylenetetramine chelant.

Conditioning Shampoo Compositions

| Components | Ex. 19 Control Wt % | Ex. 20 Wt % |
|---|---|---|
| Sodium Laureth-3 Sulfate[1] | 6.10 | 6.10 |
| Sodium Lauryl Sulfate[2] | 4.00 | 4.00 |
| Cocoamide MEA[3] | 0.90 | 0.90 |
| Guar hydroxypropyltrimonium chloride[4] | 0.25 | 0.25 |
| Glycol distearate | 1.50 | 1.50 |
| Dimethicone[5] | 1.00 | 1.00 |
| Tetrasodium EDTA dihydrate | 0.16 | 0.16 |
| Citric Acid (Anhydrous) | 0.18 | 0.18 |
| Sodium benzoate | 0.27 | 0.27 |
| Methylchloroisothiazolinone/ Methylisothiazolinone[6] | 0.0006 | 0.0006 |
| Sodium chloride | 0.20 | 0.20 |
| Hydrochloric acid (6N) | 0.06 | 0.06 |
| 2,3-Triethylenetetramine (TETA) | 0.00 | 0.10 |
| Perfume | 0.40 | 0.40 |
| Distilled Water | Q.S. | Q.S. |

[1]Sodium laureth-3-sulfate available from BASF as Standapol ES-3 (28 wt. % active).
[2]Sodium Lauryl Sulfate available from BASF as Standapol WAQ-LC (29 wt. % active).
[3]Cocamide MEA available from BASF as Comperlan CMEA (85 wt. % active).
[4]Jaguar C-500 available from Ashland.
[5]Silicone oil with viscosity of 330.000 cP
[6]Kathon CG available from Dow (1.5 wt % active).

Clarifying Shampoo Compositions

| Components | Ex. 19(a) Control Wt % | Ex. 21 Wt % |
|---|---|---|
| Sodium Laureth-3 Sulfate[1] | 6.00 | 6.00 |
| Sodium Lauryl Sulfate[2] | 9.50 | 9.50 |
| Cocamidopropyl betaine | 1.88 | 1.88 |
| Tetrasodium EDTA dehydrate | 0.16 | 0.16 |
| Citric Acid (Anhydrous) | 0.28 | 0.28 |
| Sodium benzoate | 0.25 | 0.25 |
| Methylchloroisothiazolinone/ Methylisothiazolinone[3] | 0.0005 | 0.0005 |
| Sodium chloride | 0.57 | 0.57 |
| Hydroxypropylmethylcellulose | 0.25 | 0.25 |
| 2,3-Triethylenetetramine (TETA) | 0.0 | 0.10 |
| Perfume | 0.40 | 0.40 |
| Distilled Water | Q.S. | Q.S. |

[1]Sodium laureth-3-sulfate available from BASF as Standapol ES-3 (28 wt. % active).
[2]Sodium Lauryl Sulfate available from BASF as Standapol WAQ-LC (29 wt. % active).
[3]Kathon CG available from Dow (1.5 wt % active).

Hair Repair Shampoo Compositions

| Components | Ex. 22 Control Wt % | Ex. 23 Wt % |
|---|---|---|
| Ammonium lauryl sulfate | 16.00 | 16.00 |
| Cocoamide MEA[1] | 0.8 | 0.8 |
| Cetyl alcohol | 0.9 | 0.9 |
| Polyquaternium-10[2] | 0.5 | 0.5 |
| Polyethylene glycol 7M[3] | 0.10 | 0.10 |
| Dimethicone[4] | 2.00 | 2.00 |
| Glycol distearate | 1.50 | 1.50 |

-continued

| Components | Ex. 22 Control Wt % | Ex. 23 Wt % |
|---|---|---|
| Sodium benzoate | 0.25 | 0.25 |
| Disodium EDTA | 0.13 | 0.13 |
| Citric acid | 0.04 | 0.04 |
| Sodium citrate dehydrate | 0.45 | 0.45 |
| Sodium chloride | 0.03 | 0.03 |
| Methylchloroisothiazolinone/ Methylisothiazolinone[5] | 0.0005 | 0.0005 |
| Perfume | 0.50 | 0.50 |
| 2,3-Triethylenetetramine (TETA) | 0.00 | 0.10 |
| Distilled Water | Q.S. | Q.S. |

[1]Cocamide MEA available from BASF as Comperlan CMEA (85 wt. % active).
[2]Quaternized hydroxyethyl cellulose available from Dow Unival LR30M.
[3]Available by Dow.
[4]Silicone oil with viscosity of 330.000 cP.
[5]Kathon CG available from Dow (1.5 wt % active).

Smoothing Rinse-Off Conditioner Compositions

| Components | Ex. 24 Control Wt % | Ex. 25 Wt % |
|---|---|---|
| Stearyl alcohol | 2.32 | 2.32 |
| Cetyl alcohol | 0.93 | 0.93 |
| Dicetyldimonium chloride | 0.34 | 0.34 |
| Behentrimonium methosulfate | 1.16 | 1.16 |
| Propylene glycol | 0.16 | 0.16 |
| Isopropyl alcohol | 0.28 | 0.28 |
| Disodium EDTA Dihydrate | 0.13 | 0.13 |
| Terminal amodimethicone[1] | 0.75 | 0.75 |
| Methylchloroisothiazolinone/ Methylisothiazolinone[2] | 0.0005 | 0.0005 |
| Benzyl alcohol | 0.40 | 0.40 |
| 2,3-Triethylenetetramine (TETA) | 0.00 | 0.10 |
| Distilled Water | Q.S. | Q.S. |

[1]Terminal amodimethicone with visc. Of 10,000 cP at 25° C. is available by Momentive Performance Materials.
[2]Kathon CG available from Dow (1.5 wt % active)

Volumizing Rinse-Off Conditioner Compositions

| Components | Ex. 25(a) Control Wt % | Ex. 26 Wt % |
|---|---|---|
| Hydroxypropyl guar[1] | 0.35 | 0.35 |
| DTDMAC (Quaternium-18[2]) | 0.75 | 0.75 |
| Stearamidopropyldimethylamine | 1.00 | 1.00 |
| Glyceryl monostearate | 0.25 | 0.25 |
| Emulsifying wax NF (Polywax NF) | 0.50 | 0.50 |
| Cetyl alcohol | 1.20 | 1.20 |
| Stearyl alcohol | 0.80 | 0.80 |
| Oleyl alcohol | 0.25 | 0.25 |
| Citric acid | 0.13 | 0.13 |
| EDTA | 0.10 | 0.10 |
| Terminal amodimethicone[3] | 0.50 | 0.50 |
| 2,3-Triethylenetetramine (TETA) | 0.00 | 0.10 |
| Methylchloroisothiazolinone/ Methylisothiazolinone[4] | 0.0005 | 0.0005 |
| Benzyl alcohol | 0.4 | 0.4 |
| Distilled Water | Q.S. | Q.S. |

[1]Jaguar HP-105 supplied by Rhodia
[2]Diatallowdimethylammonium chloride
[3]Terminal amodimethicone with visc. Of 10,000 cP at 25° C. is available by Momentive Performance Materials.
[4]Kathon CG available from Dow (1.5 wt % active).

Hair Repair Rinse-Off Conditioner Compositions

| Components | EX. 27 Control Wt % | EX. 28 Wt % |
|---|---|---|
| Behentrimonium chloride | 2.28 | 2.28 |
| Stearyl alcohol | 4.64 | 4.64 |
| Cetyl alcohol | 0.93 | 0.93 |
| Isopropyl alcohol | 0.57 | 0.57 |
| Disodium EDTA Dihydrate | 0.13 | 0.13 |
| Dimethicone[1] | 4.20 | 4.20 |
| Sodium hydroxide | 0.02 | 0.02 |
| Methylchloroisothiazolinone/ Methylisothiazolinone[2] | 0.0005 | 0.0005 |
| Benzyl alcohol | 0.40 | 0.40 |
| 2,3-Triethylenetetramine | 0.00 | 0.10 |
| Distilled Water | Q.S. | Q.S. |

[1]Mixture of silicone gum and silicone oil XF49-B1747 available from Momentive Performance Materials.

[2]Kathon CG available from Dow (1.5 wt % active).

Leave-On Treatment Composition

| Components | Ex. 29 Wt % |
|---|---|
| Amodimethicone and Cetrimonium chloride and Trideceth-12[1] | 0.35 |
| Polyquatemium-11[2] | 0.75 |
| PEG-40 Hydrogenated castor oil | 0.50 |
| PPG-2 Methyl ether | 0.5 |
| DMDM Hydantoin | 0.20 |
| Disodium EDTA | 0.14 |
| Poysorbate 80 | 0.12 |
| Aminomethyl propanol | 0.1 |
| Citric acid anhydrous | 0.08 |
| 2,3-Triethylenetetramine | 0.10 |
| Distilled Water | Q.S. |

[1]Siameter MEM-0949 Emulsion available from Dow Corning; it contains 35% amino-silicone

[2]Copolymer of vinylpyrrolidone and quaternized dimethylaminoethyl methacrylate; Gafquat 755 NH available by Ashland Results of Experimental Series VII Each treatment (regimen) includes cleaning with conditioning shampoo followed by a rinse-off conditioner, followed by a leave-on treatment spray (when indicated).

| Shampoo Composition (SH) | Ex. 19 Control Conditioning SH | Ex. 20 Conditioning SH | Ex. 19 Control Conditioning SH | Ex. 19 Control Conditioning SH |
|---|---|---|---|---|
| Smoothing Rinse-off conditioner composition (ROC) | Ex. 24 Control Smoothing ROC | Ex. 24 Control Smoothing ROC | Ex. 25 Smoothing ROC | Ex. 24 Control Smoothing ROC |
| Leave-on treatment composition (LOT) | No LOT | No LOT | No LOT | Ex. 29 LOT |
| Summary Description of Composition | SH Control ROC Control No LOT | SH w/chelant ROC Control No LOT | SH Control ROC w/chelant No LOT | SH Control ROC Control LOT w/chelant |
| Concentration of Chelant | 0% in SH 0% in ROC No LOT | 0.1% in SH 0% in ROC No LOT | 0% in SH 0.1% in ROC No LOT | 0% in SH 0% in ROC 0.1% in LOT |
| Chelant used | — | 2,3-Triethylenetetramine | 2,3-Triethylenetetramine | 2,3-Triethylenetetramine |
| Cycles | 20 | 20 | 20 | 20 |
| Average final copper concentration in hair (ppm) | 84 | 30 | 25 | 43 |
| Standard deviation | 5.6 | 2.1 | 1.7 | 0.2 |
| Relative content of Copper content on hair after treatment (versus control shampoo treatment) | 100 | 36 v. Treatment AM | 30 v. Treatment AM | 51 v. Treatment AM |

| Shampoo Composition (SH) | Ex. 21 Clarifying SH | Ex. 19(a) Control Clarifying SH | Ex. 23 Repair SH | Ex. 22 Control Repair SH |
|---|---|---|---|---|
| Rinse-off conditioner composition (ROC) | Ex. 25(a) Control Volumizing ROC | Ex. 26 Volumizing ROC | Ex. 27 Control Repair ROC | Ex. 28 Repair ROC |
| Leave-on treatment composition (LOT) | No LOT | No LOT | No LOT | No LOT |
| Summary Description of Composition | SH w/chelant ROC Control No LOT | SH Control ROC w/chelant No LOT | SH w/chelant ROC Control No LOT | SH Control ROC w/chelant |
| Concentration of Chelant | 0.1% in SH 0% in ROC No LOT | 0% in SH 0.1% in ROC No LOT | 0.1% in SH 0% in ROC No LOT | 0.1% in SH 0% in ROC No LOT |
| Chelant used | — | 2,3-Triethylenetetramine | 2,3-Triethylenetetramine | 2,3-Triethylenetetramine |
| Cycles | 20 | 20 | 20 | 20 |
| Average final copper concentration in hair (ppm) | 32 | 28 | 35 | 26 |
| Standard deviation | 1.6 | 3.4 | 4.5 | 0.7 |
| Relative content of Copper content on hair after treatment (versus control shampoo treatment) | 35 v. Treatment AM | 30 v. Treatment AM | 38 v. Treatment AM | 28 v. Treatment AM |

Addition of 2,3-Triethylenetetramine in any of the products of the regimen contributes to an effective removal of copper from hair after 20 conditioning shampoo/rinse-off conditioner/leave-on treatment regimen cycles compared to the corresponding treatment with control conditioning shampoo/control rinse-off conditioner. The regimen where the chelant is added in the leave-on treatment is particulary effective in removing copper form hair.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method comprising:

a. inhibiting copper deposition on hair and facilitating the removal of copper deposited on hair by applying to the hair the shampoo composition comprising:

i. from about 0.005% to about 5% of one or more chelants, by weight of the shampoo composition, wherein the one or more chelants have a molecular structure as follows:

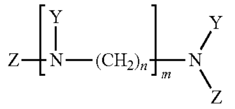

wherein n is 2 or 3; m is 1, 2, 3, or 4; and

Y and Z are independently selected from the group consisting of hydrogen, methyl, ethyl, propyl, butyl, pentyl, $—CH_2CH_2OH$, $—CH_2CH(CH_3)OH)$, $—CH_2CH_2NH_2$, $—CH_2CH(CH_3)NH_2$, and combinations thereof;

and wherein the one or more chelants comprise:

1. log of the formation constant log $K_{ML}$ of its complex with copper is higher than 6;

2. log P value is from about −5 to about 2; and 3. molecular weight of from about 50 to about 500;

ii. from about 2% to about 50% of one or more detersive surfactants, by weight of the shampoo composition; and iii. from about 75% to about 98% of an aqueous carrier, by weight of the shampoo composition;

iv. a pH of about 3 to about 8;

wherein the one or more chelants penetrates inside a hair fiber forming a copper-chelant complex;

b. rinsing the shampoo composition and the copper-chelant complex from the hair thereby removing the copper from the hair.

2. The method of claim 1, wherein the one or more detersive surfactants comprises an anionic surfactant selected from the group consisting of ammonium lauryl sulfate, include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof.

3. The method of claim 1, wherein the shampoo composition comprises from about 5% to about 25% of the one or more detersive surfactants by weight of the shampoo composition.

4. The method of claim 1, wherein the shampoo composition comprises from about 7% to about 22% of the one or more detersive surfactants by weight of the shampoo composition.

5. The method of claim 1, wherein the shampoo composition comprises from about 9% to about 18% of the one or more detersive surfactants by weight of the shampoo composition.

6. The method of claim 1, wherein the shampoo composition comprises from about 11% to about 15% of the one or more detersive surfactants by weight of the shampoo composition.

7. The method of claim 1, wherein the log P value of the one or more chelants is from about −4 to about 1.

8. The method of claim 1, wherein the log P value of the one or more chelants is from about −3 to about 0.

9. The method of claim 1, wherein the molecular weight of the one or more chelants is from about 75 to about 400.

10. The method of claim 1, wherein the molecular weight of the one or more chelants is from about 100 to about 350.

11. The method of claim 1, wherein the molecular weight of the one or more chelants is from about 125 to about 325.

12. The method of claim 1, wherein the molecular weight of the one or more chelants is from about 140 to about 300.

13. The method of claim 1, wherein the shampoo composition further comprises a gel network, wherein the gel network comprises a fatty alcohol and a surfactant.

14. The method of claim 1, wherein the shampoo composition comprises from about 0.01% to about 3% of the one or more chelants.

15. The method of claim 1, wherein the shampoo composition comprises from about 0.01% to about 1% of the one or more chelants.

16. The method of claim 1, wherein the shampoo composition comprises from about 0.01% to about 0.5% of the one or more chelants.

17. The method of claim 1, wherein the shampoo composition comprises from about 0.01% to about 0.1% of the one or more chelants.

18. The method of claim 1, wherein the one or more chelants are selected from the group consisting of 2,3-triethylenetetramine, tetraethylenepentamine, 2,4-tetraethylenepentamine, pentaethylenehexamine, tris(2-aminoethyl) amine, ethylenedinitrilotetrapropan-2-ol, 1,1',1",1'"[2-hydroxypropyl)imino]bis(2,1ethanediylnitrilo)]tetrakis-2-propanol, tetraethylenepentaamine-(1-EO), 1,5,9,13-Tetraazatridecane, and mixtures thereof.

19. A method comprising:

a. inhibiting copper deposition on hair and facilitating the removal of copper deposited on hair by applying to the hair the shampoo composition comprising:

i. from about 0.01% to about 1%, by weight of the composition, of a chelant wherein the chelant consists of 2,3-Triethylenetetramine;

ii. from about 5% to about 25% of one or more detersive surfactants, by weight of the shampoo composition;

iii. a cationic polymer;

iv. a silicone;

v. from about 75% to about 98% of an aqueous carrier, by weight of the shampoo composition;

vi. a pH of about 3 to about 8;

wherein the chelant penetrates inside a hair fiber forming a copper-chelant complex;

b. rinsing the shampoo composition from the hair and the copper-chelant complex from the hair thereby removing the copper from the hair.

20. The method of claim 19 wherein the one or more detersive surfactants comprises ammonium lauryl sulfate; and wherein the cationic polymer comprises Polyquaternium-10.

* * * * *